US00PP29091P3

(12) United States Plant Patent
Grosser

(10) Patent No.: US PP29,091 P3
(45) Date of Patent: Mar. 13, 2018

(54) MANDARIN TREE NAMED 'N40W-6-3'

(50) Latin Name: ***Citrus reticulata* Blanco hybrid**
Varietal Denomination: N40W-6-3

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 61 days.

(21) Appl. No.: 14/756,644

(22) Filed: Sep. 28, 2015

(65) Prior Publication Data

US 2017/0094855 P1 Mar. 30, 2017

(51) Int. Cl.
*A01H 5/08* (2006.01)

(52) U.S. Cl.
USPC ..... Plt./202

(58) Field of Classification Search
USPC ..... Plt./156, 201, 202
See application file for complete search history.

(56) References Cited

U.S. PATENT DOCUMENTS

PP21,356 P3 10/2010 Gmitter, Jr. et al.
PP23,724 P2 7/2013 McCollum et al.
PP26,086 P3 11/2015 Grosser

OTHER PUBLICATIONS

*Citrus* Industry. Aug 2013. Jump on the Fast Track: New fresh *Citrus* varieties from the University of Florida. http://www.crec.ifas.ufl.edu/extension/trade_journals/2013/2013_August_fast.pdf. Accessed Apr. 4, 2017. 6 pages.*
U.S. Appl. No. 14/757,086, filed Nov. 16, 2015, Chaparro.
U.S. Appl. No. 14/544,780, filed Feb. 12, 2015, Gmitter.
Hearn, "Development of seedless grapefruit cultivars through budwood irradiation," *J Amer Soc Hort Sci* 111 : 304-306, 1986.

* cited by examiner

*Primary Examiner* — June Hwu
*Assistant Examiner* — Karen Redden
(74) *Attorney, Agent, or Firm* — Dentons US LLP

(57) ABSTRACT

A new hybrid mandarin tree particularly distinguished by producing seedless tangerine fruit from October to December in Central Florida is disclosed.

4 Drawing Sheets

Latin name of the genus and species of the plant claimed: *Citrus reticulata* Blanco hybrid.

Variety denomination: 'N40W-6-3'.

BACKGROUND OF THE INVENTION

The present invention relates to a new and distinct, nearly seedless variety of hybrid mandarin (tangerine) for the fresh *citrus* market named 'N40W-6-3'. 'N40W-6-3' was selected from a population of 50 plants grown from irradiated budwood (cobalt 60, Vindicator Co., Mulberry, Fla.) from 'Snack' (unpatented), a seedy mandarin hybrid of unknown parentage. Irradiation treatment of budwood is known to induce mutations that, in rare instances, cause a permanent genetic change in a variety to greatly reduce or eliminate seed in fruit, without otherwise altering the integrity of the variety. 'N40W-6-3' was first asexually propagated by grafting to experimental rootstock Orange #14 (unpatented) and planted in Lake Alfred, Fla., in 2011. Asexually propagated trees of 'N40W-6-3' have remained true-to-type to the original selection through successive generations.

SUMMARY OF THE INVENTION

'N40W-6-3' produces small to medium seedless (or nearly seedless) fruit with a unique and robust sweet flavor, and should compete favorably with the 'Fall-Glo' (unpatented), a mandarin hybrid in the fall fresh mandarin market. 'N40W-6-3' is distinct from 'Fall-Glo' in a number of ways, including, but not limited to, the following:

- Fruit size and firmness: 'N40W-6-3' fruit is generally smaller and firmer than that of 'Fall-Glo'.
- Fruit flavor profile, aroma, and acidity: 'N40W-6-3' and 'Fall-Glo' fruit have different flavor profiles and aroma. For instance, the fruit of 'Fall-Glo' can be tart during early harvest due to higher acidity; whereas, the fruit of 'N40W-6-3' is less tart throughout the harvest period as it is less acidic.
- Seed number in fruit: 'N40W-6-3' is nearly seedless; whereas 'Fall-Glo' is a seedy variety. 'N40W-6-3' fruit seed number also distinguishes it from variety 'Snack', which averages more than 16 seeds per fruit.

'N40W-6-3' harvest can begin in October, but the fruit reaches maximum flavor and quality around the last two weeks of November. Fruit of 'N40W-6-3' can be peeled, however it should not be considered a zipper-skinned tangerine selection. Fresh juice obtained from fruit of 'N40W-6-3' also has outstanding flavor, but fruit quality data is only available from trees grown on 'Swingle' (unpatented) citrumelo rootstock. The exceptional juice flavor did not hold up during processing. A portion of the first-year crop can exhibit a rougher rind and lower juice content, although this diminishes with subsequent crops. 'N40W-6-3' makes a small compact tree when grown on 'Swingle' citrumelo rootstock. Trees appear to yield adequately, although no formal yield data is available at this time. Fruit size is generally smaller with heavy crops.

BRIEF DESCRIPTION OF THE DRAWINGS

'N40W-6-3' is illustrated by the accompanying photographs which show the plant's form, foliage, and fruit. The colors shown are as true as can be reasonably obtained by conventional photographic procedures. Tree and leaf photographs were taken in November of 2010, and fruit photographs were taken in January of 2011.

DETAILED BOTANICAL DESCRIPTION

Figure 1:
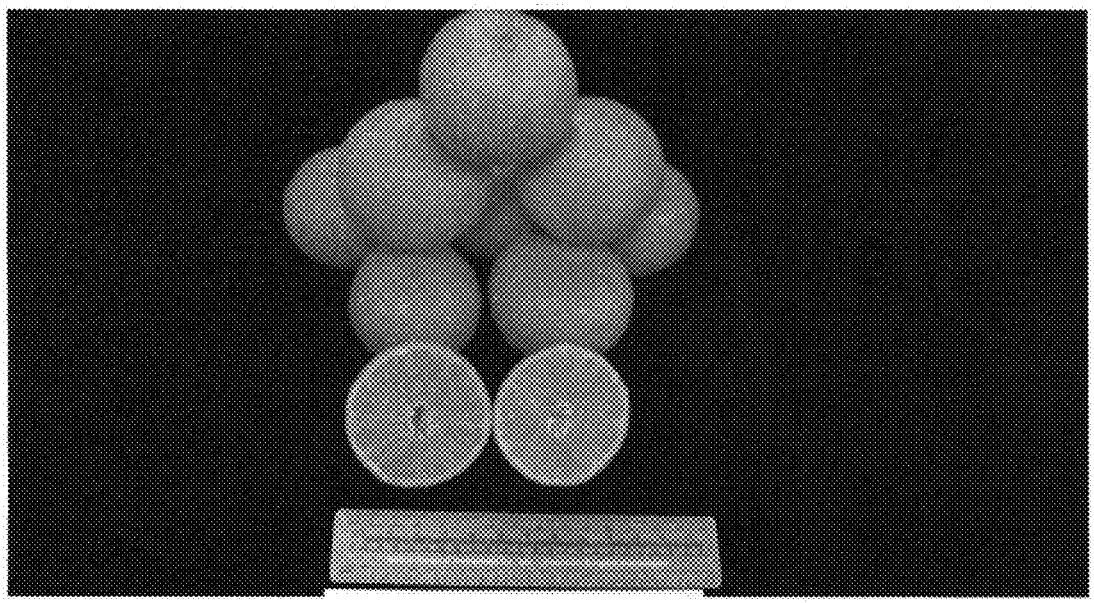
FIG. 1—Shows whole and cut fruit of 'N40W-6-3'.
Figure 2:
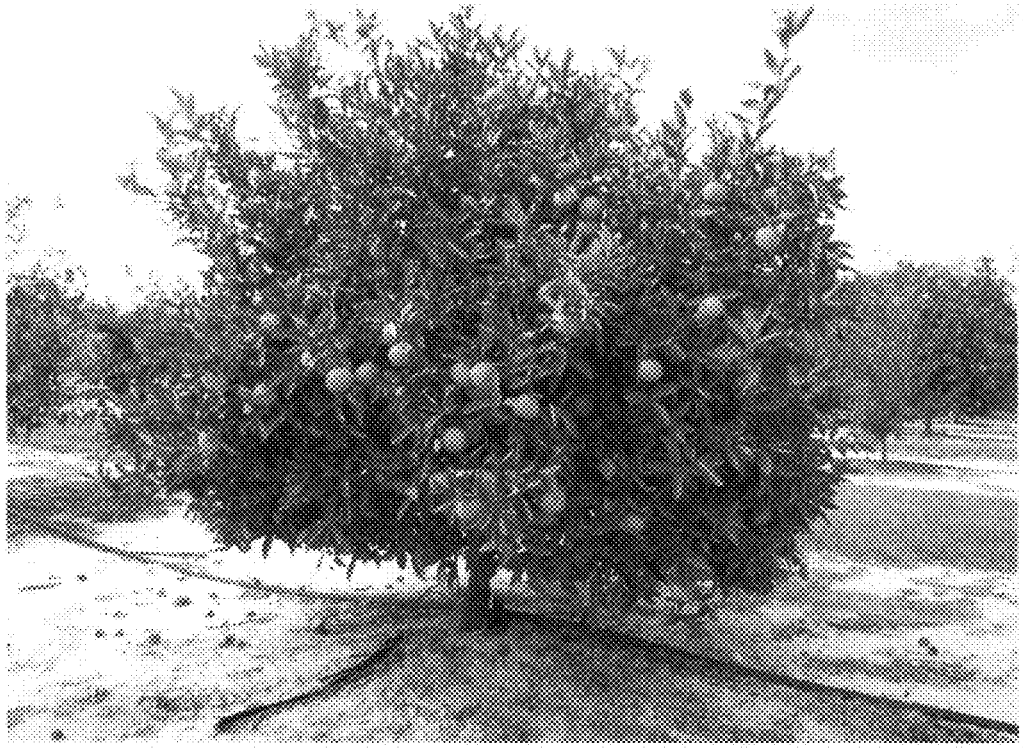
FIG. 2—Shows an approximately 8-year-old tree of 'N40W-6-3', showing plant habit, including foliage and fall fruit.
Figure 3:
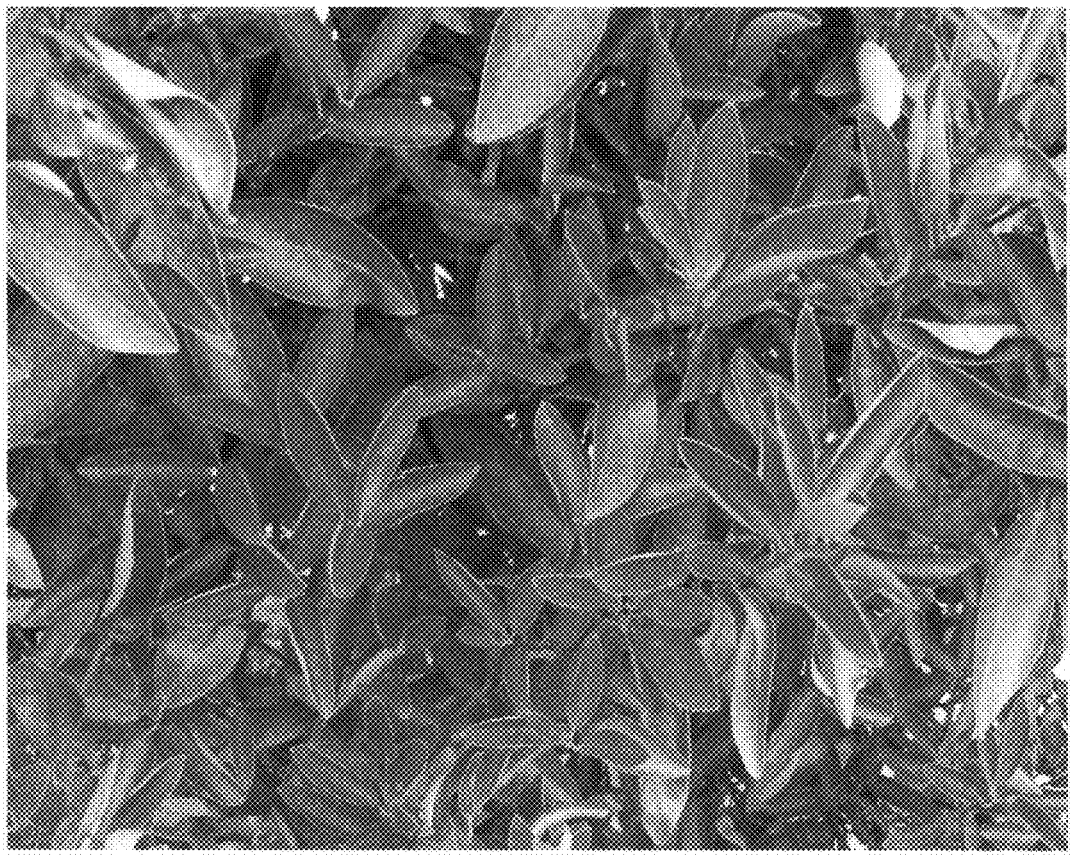
FIG. 3—Shows a close-up of 'N40W-6-3' twigs and mature leaves from an approximately 8-year-old tree.
Figure 4:
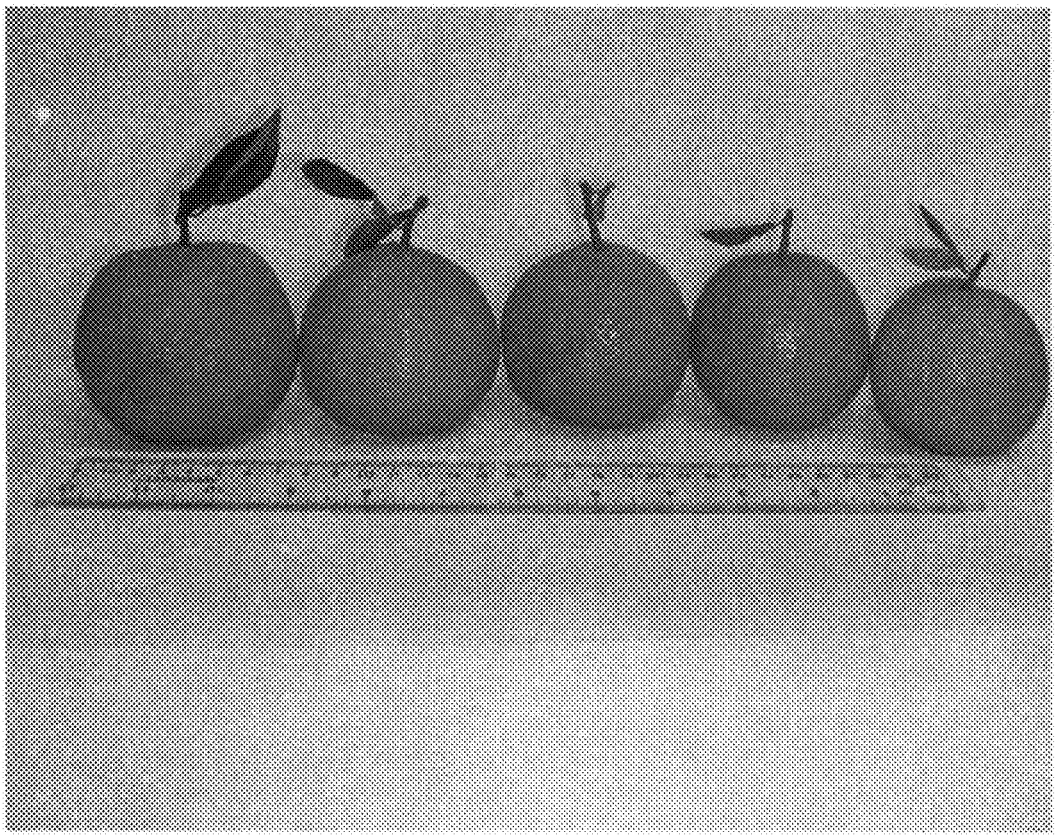
FIG. 4—Shows mature fruit of 'N40W-6-3' demonstrating typical rind color and shape.

The following detailed description sets forth the distinctive characteristics of 'N40W-6-3'. The present botanical description is that of the variety grown on 7-year-old trees growing on 'Swingle' rootstock in Lake Alfred, Fla. The colors (except those in common terms) are described from The Royal Horticultural Society (R.H.S.) Colour Chart (second edition) published by The Royal Horticultural Society in London in association with the Flower Council of Holland.

Phenotypic Description of *Citrus Reticulata* Blanco 'N40W-6-3'

Classification:

*Botanical.*—*Citrus reticulata* Blanco.

*Common name.*—Mandarin hybrid or Tangerine.

Progenitor variety: 'Snack' (*Citrus reticulata* Blanco, unpatented with unknown parentage).

Tree:

*Ploidy.*—Diploid.

*Size.*—Compacted, medium-small size with heights of 1.8 to 1.9 m, currently unpruned.

*Height.*—1.8 to 1.9 m unpruned.

*Tree spread.*—1.8 to 2.0 m.

*Vigor.*—Moderately vigorous growth; normally growing shoots of 0.2 to 0.3 m, typically from new flush on current tree.

*Density.*—Canopy is quite dense. Branches are quite compact on the tree canopy, resulting in a small tree.

*Form.*—The shape of the tree is obloid with upright branches. Branches exhibit very little drooping with fruit.

*Growth habit.*—Compact and upright.

Trunk:

*Trunk diameter.*—14.6 cm at 30 cm above the ground.

*Trunk texture.*—Smooth.

*Trunk bark color.*—RHS 197A (greyed-green), irregularly striated with RHS N189A (greyed-green) and RHS 189A (greyed-green).

Branches:

*Crotch angle.*—Major branches form a 40- to 45-degree crotch angle.

*Branch length.*—1.2 to 1.6 m.

*Branch texture.*—Relatively smooth and without thorns or spines.

*Branch color* (*shoots from previous flush, hardened, and* 4 *to* 5 *mm in diameter*).—RHS 138A (green).

Leaves:

*Size* (*lamina average*).—Length: 67 mm. Width: 30 mm. L/W ratio: 2.2.

*Arrangement.*—Alternate.

*Thickness.*—Regular and average for commercial mandarin hybrids.

*Type.*—Simple.

*Shape.*—Elliptical.

*Apex.*—Slightly retuse.

*Base.*—Acute to sub-obtuse.

*Margin.*—Entire; smooth and very slightly undulate.

*Surface.*—Upper surface: Glabrous. Lower surface: Medium veins that are pinnately netted.

*Venation pattern.*—Pinnate.

*Venation color.*—Upper surface: RHS 138D (green). Lower surface: RHS 138A (green).

*Color.*—Young Upper surface (adaxial): RHS 137A (green). Young Lower surface (abaxial): RHS 138B (green). Mature Upper surface (adaxial): RHS 139A (green). Mature Lower surface (abaxial): RHS 137C (green).

*Petiole.*—Shape: Brevipetiolate (shorter than leaf lamina); junction between petiole and lamina is articulate. Width (petiole wing): Very narrow. Shape (petiole wing): Obovate. Length: 6 to 8 mm. Width: 1 to 1.5 mm. Color: RHS 137A (green).

Flowers and flower buds:

*Type.*—Hermaphroditic.

*Flower blooming period.*—First bloom observed: Late March, in Central Florida. Full bloom observed: Early April, in Central Florida.

*Flower petals.*—Number: 5. Color: RHS 155B (white) with RHS 150A (yellow-green) spots distributed at the back side of the petal. Length: 13 mm. Width: 4 mm. Calyx: Small to medium sized.

*Fragrance.*—Fragrant compared to other *citrus* blossoms.

*Reproductive organs.*—Fertility: Self-fertile. Stamen number: 3 per petal. Anther color: RHS 12B (yellow). Anther filament length: Shorter relative to stigma. Pollen amount: Moderately abundant. Pollen color (general): RHS 12C (yellow).

Fruit:

*Size.*—Uniform.

*Height.*—60 to 65 mm.

*Width.*—65 to 75 mm; some fruits reach 85 mm.

*Average weight* (*per individual fruit*).—136.6 g

*Shape.*—Round.

*Shape* (*cross-section*).—Round.

*Apex.*—Truncated and slightly depressed.

*Apex cavity diameter.*—8-10 mm, usually filled with pithy material.

*Base.*—Flat with wrinkles, occasionally some fruit have a very short neck.

*Harvesting period.*—October to December.

Skin:

*Adherence.*—Albedo (mesocarp) to flesh (endocarp) is medium-low, compared to other commercial hybrid varieties; not a zipper-skin, but can be peeled cleanly.

*Thickness.*—2.0 to 3.0 mm.

*Texture.*—Pitted.

*Color*.—Flavedo (epicarp): Variable, the flavedo of an individual fruit becomes darker as the season progresses, advancing from RHS 25A (orange) to RHS 25B (orange), and finally to RHS 28A (orange-red). Albedo (mesocarp): RHS 24C (orange).

*Stylar end*.—Closed.

*Rind oil cell density*.—68 to 74 oil cells per square centimeter.

*Average size of fruit surface oil glands*.—Very small, 0.5-0.7 mm in diameter.

Flesh:

*Number of segments*.—10 to 12 segments per fruit on average.

*Average length of a fruit segment*.—23-25 mm.

*Average diameter of a fruit segment*.—16-19 mm.

*Segment walls*.—Thin with sufficient strength to maintain integrity as separated.

*Color*.—RHS 25B (orange).

*Juice*.—Abundant.

*Juice color number*.—41.5 (Juice color number is an industry standard measurement of *citrus* juice color that can be obtained using a HunterLab Model D45 *Citrus* Colorimeter for which the *Citrus* Red (CR) and *Citrus* Yellow (CY) has been calibrated with USDA orange juice standard color tube No 4; USDA grade "A" orange juice requires a juice color number of at least 36. Juice color number is calculated using the following formula: 22.510+(0.165)*CR+(0.111)*CY.).

*Texture*.—Melting flesh.

*Vesicles*.—Length: 6 to 15 mm. Diameter (thickness): 3 to 4 mm.

*Eating quality* (*varies from season to season*).—Excellent unique, sweet, but robust flavor (data from fruit harvested Nov. 22, 2010). Fruit generally reaches legal maturity in October, but reaches peak flavor around the end of November. Juice has excellent flavor when fresh squeezed, although flavor does not hold up during processing.

*Total soluble solids* (*average*).—12.03° Bx.

*Titratable acidity* (*average*).—0.59 grams of citric acid per 100 mL of juice.

*Ratio*.—20.39.

Seeds:

*Type*.—Polyembryonic.

*Number*.—Ranges from 0 to 1. Most of the fruit contain 0 seeds or undeveloped seed. Occasionally some fruit contain 1 seed (compared to the original 'Snack' selection, which contains approximately 16 seeds per fruit).

*Shape*.—Normal seed are mostly obclavate and club shaped.

*Size*.—Length: 13.0 mm. Width: 6.0 mm.

*Seed coat color*.—Outer Surface: RHS 159C (orange-white) and smooth. Inner surface: RHS 165C (greyed-orange). Cotyledon color: RHS 138C (green).

Resistance to disease: Resistant to *citrus* canker. Trees are susceptible to HLB (Huanglongbing or *citrus* greening disease), but show reasonable tolerance and sustained production if grown under an optimized nutrition program, particularly CRF (controlled-release fertilizer) containing high levels of manganese and boron.

What is claimed is:

1. A new and distinct *citrus* rootstock cultivar as illustrated and described herein.

* * * * *